US012616660B2

(12) United States Patent
Boit et al.

(10) Patent No.: US 12,616,660 B2
(45) Date of Patent: *May 5, 2026

(54) COMPRESSIBLE AND FREE-FLOW CO-AGGLOMERATES OF CRYSTALLINE MANNITOL AND GRANULAR STARCH

(71) Applicant: ROQUETTE FRERES, Lestrem (FR)

(72) Inventors: Baptiste Boit, Lestrem (FR); Alain Francois, Hinges (FR); Philippe Lefevre, Haverskerque (FR); Damien Passe, Douai (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,990

(22) Filed: Sep. 24, 2021

(65) Prior Publication Data

US 2022/0008343 A1     Jan. 13, 2022

Related U.S. Application Data

(60) Continuation of application No. 16/748,222, filed on Jan. 21, 2020, now Pat. No. 11,364,204, which is a continuation of application No. 15/620,399, filed on Jun. 12, 2017, now abandoned, which is a division of application No. 13/318,211, filed as application No. PCT/FR2010/050813 on Apr. 28, 2010, now Pat. No. 9,937,131.

(30) Foreign Application Priority Data

Apr. 30, 2009     (FR) ...................................... 0952894

(51) Int. Cl.
*A61K 9/20*     (2006.01)
*A61K 9/48*     (2006.01)

(52) U.S. Cl.
CPC .......... *A61K 9/2018* (2013.01); *A61K 9/2059* (2013.01); *A61K 9/4858* (2013.01); *A61K 9/4866* (2013.01)

(58) Field of Classification Search
None
See application file for complete search history.

(56) References Cited

U.S. PATENT DOCUMENTS 3,145,146 A      8/1964    Lieberman et al.
6,235,947 B1 *   5/2001    Yoshinari ................ C07C 29/78
                                                         546/342
6,664,389 B1 *   12/2003   Shi .......................... C08B 30/12
                                                         127/65
6,743,447 B2     6/2004    Labergerie et al.
9,839,610 B2     12/2017   Boit et al.
9,937,131 B2     4/2018    Boit et al.
2003/0114717 A1  6/2003    Erdmann et al.
2004/0180085 A1  9/2004    Ohkouchi et al.
2006/0141044 A1 * 6/2006   Gustafsson .......... A61K 31/216
                                                         514/534

FOREIGN PATENT DOCUMENTS

EP     0 933 079 A1    8/1999
EP     1 138 661 A1    10/2001
EP     1 153 616 A1    11/2001
JP     61-85331 A      4/1986
JP     09077669 A      3/1997
JP     10-158153 A     6/1998
WO     00/47233 A1     8/2000

OTHER PUBLICATIONS

Shirsand et al. "Design and evaluation of fast dissolving tablets of clonazepam", Indian Journal of Pharmaceutical Science, Nov.-Dec. 2008.*
The Farber et al. "Evaluation and structure of drying material bridging of pharmaceutical excipients: studies on microscope slide", Chemical Engineering Science, 58 4515-4525 (Year: 2003).*
Hulse et al. "The characterization and comparison of spray-dried mannitol samples", Drug Development and Industrial Pharmacy; 35(6); 712-718 (Year: 2009).*
Hulse et al. The characterization and comparison of spray-dried mannitol samples, Drug Development and Industrial Pharmacy; 35(6); 712-718 (Year: 2009) (Year: 2009).*
Nov. 18, 2021 Office Action issued in U.S. Appl. No. 16/748,222.
Feb. 8, 2019 Office Action issued in U.S. Appl. No. 15/620,399.
Aug. 19, 2019 Office Action issued in U.S. Appl. No. 15/620,399.
Sep. 26, 2018 Office Action issue in U.S. Appl. No. 15/620,399.
French Search Report, dated Dec. 15, 2009.
Bouffard et al., "Influence of process variable and physicochemical properties on the granulation mechanism of mannitol in a fluid bed top spray granulator", Drug Development and Industrial Pharmacy, 31:923-933, 2005.
Jivraj et al., "An overview of the different excipients useful for direct compression of tablets", PSTT vol. 3, No. 2, Feb. 2000.
Database CA [Online] Chemical Abstracts Service, Columbus, Ohio, US; May 22, 1997 (May 22, 1997), Asogawa, Tatsuo et al: "Vitamin B granules" XP002560481, retrieved from STN, Database accession No. 997:326257 abstract.
Database WPI Week 199722, 1997 Thomson Scientific, London, GB; AN 1997-241649, XP002560482 "Vitamin B granules."
Database WPI Week 198624, 1986 Thomson Scientific, London, GB; AN 1986-152485 XP002560483.

(Continued)

*Primary Examiner* — Isis A Ghali
(74) *Attorney, Agent, or Firm* — Oliff PLC

(57) ABSTRACT

Coagglomerates of crystalline mannitol and granular starch have a laser mean volume diameter D4,3 of between 60 and 500 μm, a ratio of mannitol/starch is between 99.5/0.5 and 50/50, and the mannitol is both in the alpha and beta crystalline forms.

9 Claims, No Drawings

(56) References Cited

OTHER PUBLICATIONS

International Search Report, dated Jul. 23, 2010.
Pharmacopee Europeenne 5.0, Tome 1, Jan. 2005:20916, paragraphe 2.9.16.
Pharmacopee Europeenne 5.0, vol. 1, 0112005:20915, paragraphe 2.9.15.
"Oral Solid Dosage Forms," Remington Farmacia, Tomo I, 20 Edicion Buenos Aires Editorial Medica Panamericana, 2003 pp. 1011 and 1020.

* cited by examiner

COMPRESSIBLE AND FREE-FLOW CO-AGGLOMERATES OF CRYSTALLINE MANNITOL AND GRANULAR STARCH

A subject matter of the present invention is coagglomerates of crystalline mannitol and of granular starch which exhibit an outstandingly high tableting capacity, which marks them out very particularly for the preparation of tablets.

The invention also relates to coagglomerates of crystalline mannitol and of granular starch exhibiting an excellent ability to flow, which also marks them out for use in the filling of hard gelatin capsules.

Finally, the invention relates to the process which makes it possible to obtain these coagglomerates.

In the field of the use of polyols, as regards the field with which the present invention is specifically concerned, namely pharmaceutical excipients and bulk sweeteners used in the food industry, several pulverulent polyols are commonly used. They are sorbitol, xylitol and especially mannitol.

The pharmaceutical industry consumes large tonnages of mannitol. The latter is used in particular as excipient in the dry forms, which are, for example, powders for filling hard gelatin capsules, powders for a sachet to be dispersed or dissolved at the time of use in water, solid oral forms and tablets.

This is because mannitol, due to its flavor and the very low hygroscopicity of its crystalline form, constitutes an excellent excipient, in particular for its very high chemical inertia with regard to the active principles.

Unfortunately, the product obtained by crystallization in the water from a supersaturated solution is not naturally compressible.

In order to remedy this situation, it is known by experts in the field to add a binder in order to increase its tableting capacity.

U.S. Pat. No. 3,145,146 describes, for example, a process consisting in using paraffin wax, gum or a cellulose derivative as binder before the step of spray-drying resulting in the preparation of the mannitol powder.

However, this technical solution is not prized by the user.

It is known by a person skilled in the art, for the preparation of hard gelatin capsules, that the mixtures capable of being used for the filling of hard gelatin capsules have to be able to lend themselves to automatic filling, in order to guarantee a uniform dosage.

It is obvious that a pharmaceutical dosage formulation operation is necessary for some substances, in order to ensure uniform and exact filling on very high speed machines.

Care should in particular be taken with regard to the following parameters:

shape and size of the particles,
uniform particle size,
homogeneity of the mixture,
flow property of the powder,
moisture level,
good agglomeration under pressure.

In point of fact, next to its non tableting capacity, it is necessary to add another disadvantage of the mannitol obtained by crystallization in water, which is that it exhibits mediocre flow properties due to the orthorhombic structure of its crystals and in particular due to its excessive friability.

This friability results in the formation of fine particles which interfere in particular with its flow properties, especially during the filling and the emptying of the hoppers and chutes for feeding the devices employed to manufacture tablets or to fill hard gelatin capsules.

For this reason, the mannitol crystallized in water is certainly not an excipient of choice which can be used in the filling of hard gelatin capsules.

Here again, it is necessary to add a binder.

In the U.S. Pat. No. 3,145,146, the addition of binder does not, however, prevent at least 50% of the particles of the powder from still having a size of less than 75 μm, which is far from being ideal in producing good flow.

In the field of tablets, starch can advantageously be used as binder when it is subjected to a precooking and can also act as diluent.

Furthermore, it has good disintegrating properties due to its hydrophilicity in water when it is employed in the granule form.

However, it has to be incorporated in a high amount, generally of greater than 15% of the final formulation.

On the other hand, it exhibits, due to the small size of its particles and its low density, the disadvantage of not flowing.

The high elasticity of its granules furthermore confers a very poor tableting capacity on it, which does not make possible the manufacture of tablets of satisfactory hardness.

A person skilled in the art thus cannot envisage combining mannitol and granular starch in order to take advantage of the binding properties of the starch for providing the mannitol with the tableting capacity or flow properties which are lacking in it.

In fact, if the combination of starch and mannitol was practiced, it is rather in the field of the manufacture of orodispersible tablets, where it has been in particular a matter of taking advantage of the disintegrating and diluting properties of the starch.

For example, a description is given, in patent application WO 00/47233, of a preparation for tablets comprising the physical mixture of an active ingredient and a starch with in particular mannitol.

In point of fact, it is strongly recommended in this patent application to add, to this physical mixture, one or more lubricants chosen from magnesium stearate, calcium stearate, sodium stearyl fumarate and light silicic anhydride in order to facilitate the flow of said mixtures in the items of equipment for the manufacture of tablets.

A description is given, in patent application JP 09.077669, of a physical mixture comprising mannitol, starch and vitamin C. Said physical mixture is dried by a conventional spray-drying process, that is to say an spray-drying of single effect type without recycling of the fine particles. This results in a powder of relatively low tableting capacity exhibiting poor flow.

It thus appears difficult to provide a single solution which makes it possible to reconcile both the tableting capacity properties and the ability to flow of a crystalline mannitol powder, and this is to run counter to a technical preconception, that of providing a solution consisting in using an agglomerate of mannitol and of granular starch.

Thus it is that even the Applicant Company, in its patent EP 1 138 661, succeeded in conferring, on a crystalline mannitol of fine particle size, an excellent ability to flow but failed to accord it properties of tableting capacity.

The pulverulent mannitol obtained according to said patent EP 1 138 661 had thus been exemplified in the formulation of a powder for filling hard gelatin capsules but the filling had had to be simulated on a device specially designed for the experiment.

The aim of the invention is thus to overcome these disadvantages and the Applicant Company has had the credit of finding, after numerous studies, that this aim could be achieved as soon as use is made of coagglomerates based on granular starch and mannitol.

The term "granular starch" is understood to mean native starches of any origin, natural or hybrid, of granular type and all chemically modified starches which have retained the granular form.

Use will preferably be made of a white corn starch, such as that sold by the Applicant Company under the name "extra white starch", which makes it possible to obtain granules with an entirely satisfactory whiteness.

Another subject matter of the invention is coagglomerates of crystalline mannitol and of granular starch, characterized in that they make possible:

the preparation, by direct tableting, of tablets exhibiting noteworthy properties of hardness,
the filling of hard gelatin capsules for the preparation of which it is not necessary to use large amounts of lubricant and of flow agents in order to facilitate the filling and the emptying of the hoppers and chutes for feeding the devices employed.

A subject matter of the invention is thus the use of the coagglomerates of crystalline mannitol and of granular starch where the granular starch participates in the tableting capacity of said agglomerate and facilitates the lubrication, such properties of the granular starch which a person skilled in the art did not expect to find.

Finally, a subject matter of the invention is:

tablets
hard gelatin capsules
comprising coagglomerates of crystalline mannitol and of granular starch where the granular starch acts both as binder and as lubricant.

A subject matter of the invention is more particularly coagglomerates of crystalline mannitol and of granular starch, wherein:

the tableting capacity, determined according to a test A, is greater than 120 N, preferably between 200 and 450 N and more preferably still between 220 and 400 N,
the flow grade, determined according to the test B, is between 3 and 15 seconds, preferably between 4 and 8 seconds and more preferably still between 4 and 6 seconds.

The coagglomerates according to the invention are characterized by their tableting behavior, determined according to a test A.

The test A consists in measuring the force, expressed in newtons, which is necessary to bring about the crushing of a tablet prepared using a Frogerais AM laboratory alternating press sold by Sviac (France) starting from said coagglomerate lubricated with 1.2% of magnesium stearate (lubrication carried out by mixing the coagglomerate and the magnesium stearate for 5 minutes in a Turbula T2C mixer from Willy A. Bachofen), thus reflecting the crushing strength of the tablet, which is cylindrical with convex faces and which has a diameter of 13 mm, a thickness of 6 mm and a weight of 0.734 g, i.e. with a bulk density of 1.3 g/ml. This force, expressing the hardness of the tablet and consequently the tableting capacity of the powder, is measured on an Erweka TBH 30 GMD hardness tester. The value given in newtons corresponds to a mean produced with 10 measurements.

The coagglomerates according to the invention then exhibit a tableting capacity, determined according to test A, of greater than 120 N, preferably of between 200 and 450 N.

As the starch has a very poor tableting capacity, it is surprising to find that said coagglomerates of mannitol and of starch exhibit a high tableting capacity which makes it possible to produce tablets which, although additionally comprising pharmaceutical, veterinary or nutraceutical active ingredients, or foodstuffs or excipients, flavorings or colorants, will retain a sufficient hardness for the subsequent handling thereof, whether film coating, packaging in blister packs, packaging in tubes or indeed even bulk packaging.

A high tableting capacity is also desired for the filling of the hard gelatin capsules, in particular on industrial capsule-filling machines using the principles of the dosator or of the dosing disk.

The coagglomerates according to the invention are also characterized by their ability to flow, determined according to test B.

The test B consists in determining the time necessary for the flow of 100 g of powder according to the measurement method recommended by the European Pharmacopoeia (EP 5.0, volume 1, January 2005: 20916, section 2.9.1.6; equipment according to FIG. 2.9.16.-2).

The coagglomerates according to the invention then exhibit a flow grade, determined according to the test B, of between 3 and 15 seconds, preferably of between 4 and 8 seconds.

The coagglomerates exhibit an excellent free flow, whereas the granular starch does not flow freely and whereas the physical mixtures of mannitol and starch do not flow or flow only very slightly.

The coagglomerates according to the invention exhibit a laser volume mean diameter D4,3 of between 60 and 500 μm, preferably of between 100 and 250 μm.

The particle size distribution values are determined on a laser diffraction particle sizer of LS 200 type form Beckman-Coulter, equipped with its powder dispersion module (dry route), following the technical handbook and the specifications of the manufacturer.

The operating conditions of screw speed under the hopper and of intensity of vibration of the dispersing chute are determined so that the optical concentration is between 4% and 12%, ideally 8%.

The measurement range of the laser diffraction particle sizer of LS 200 type is from 0.04 μm to 2000 μm. The results are calculated as % by volume and expressed in μm.

The particle size distribution curve also makes it possible to determine the value of the volume mean diameter (arithmetic mean) D4,3.

In the tablets and the hard gelatin capsules comprising active ingredients, the homogeneity in the dosage of active ingredients is obtained by optimizing the mean diameter of the excipients with respect to the mean diameter of the active ingredients, generally, without this being systematic, by bringing these mean diameters closer together.

The coagglomerates according to the invention provide access to mean diameters corresponding to the majority of active ingredients, from 60 to 500 μm, both for preparing tablets and for filling hard gelatin capsules.

The coagglomerates according to the invention are also characterized in that the mannitol/starch ratio is between 99.5/0.5 and 50/50 and preferably between 95/5 and 70/30.

Above 99.5% of mannitol or below 50% of mannitol, the Applicant Company has found that said coagglomerates do not have satisfactory properties of tableting capacity or of flow.

Preferably, a ratio of mannitol to starch of between 95/5 and 70/30 is chosen.

According to another embodiment of the invention, the coagglomerates comprise mannitol and starch and can furthermore comprise any appropriate additive provided that it does not interfere with the properties desired for the final granules, such as, in particular, flavorings, colorants, stabilizers, binders, lubricants or preservatives.

They can also be pharmaceutical or plant-protection active ingredients or detergents.

The coagglomerates in accordance with the invention exhibit:

a aerated density of between 0.400 and 0.750 g/ml, preferably of between 0.450 and 0.650 g/ml, and a tapped density of between 0.500 and 0.850 g/ml, preferably of between 0.550 and 0.750 g/ml.

The aerated and tapped densities of the coagglomerates in accordance with the invention are the aerated and tapped bulk densities determined according to the measurement method recommended by the European Pharmacopoeia (EP 5.1, Volume 1, January 2005: 20915, section 2-9-15; equipment according to FIG. 2-9-15-1), the tapped bulk density being obtained after 1250 taps.

High tapped densities are desired in order to reduce the volume of the tablets and hard gelatin capsules to be swallowed and thus to improve the observance of the medication by the patients.

Nevertheless, homogeneity in mixing between the coagglomerates and the powder formed of active ingredients often requires a similarity in the aerated densities. It is therefore necessary for the coagglomerate to be more or less dense according to the active ingredient to be incorporated.

The coagglomerates according to the invention can exhibit densities over a broad range which are suitable for the majority of cases.

The coagglomerates of crystalline mannitol and of granular starch according to the invention are finally characterized in that the mannitol is provided both in the alpha and beta crystalline forms.

Mannitol is conventionally sold in three crystalline forms: alpha, beta and delta, the beta form being the form most commonly used as it is more stable.

This is because it is very generally known that mannitol of alpha or delta crystalline form, brought into the presence of a small amount of water, is unstable as it dissolves and then recrystallizes in the beta form.

The Applicant Company was thus in opposition to a technical preconception which considers that the beta crystalline form should be preferred to the alpha form, in particular in applications where the risk of a recrystallization of the alpha form to give the beta form is harmful, for example to the ability of tablets comprising it to disintegrate in the mouth or in attempting to optimize the properties of tableting capacity or the ability to flow of the mannitol.

The coexistence of the two alpha and beta crystalline forms of mannitol can be determined conventionally by any method furthermore known to a person skilled in the art, i.e. by infrared spectrometry or by X-ray diffraction.

By infrared spectrometry, the method commonly used is that of the potassium bromide pellet. The two crystalline forms of mannitol then exhibit a different profile.

In places, the differences are more or less marked; the spectral region studied is thus located between 2850 and 3050 cm$^{-1}$; the alpha form is characterized by the presence of an adsorption band at approximately 2885 cm$^{-1}$ and the beta form, for its part, is characterized by those at approximately 2985 and 2900 cm$^{-1}$.

The mixtures of these two forms will then show more or less pronounced differences according to the proportions of the two forms and the spectral region studied.

By virtue of measurements carried out on standard mixtures of alpha and beta crystalline forms, it is relatively easy to quantify the proportions of crystalline forms in the coagglomerates of crystalline mannitol and of granular starch according to the invention, as will be seen in the examples below.

These values can be confirmed by X-ray diffraction spectrometry.

This is because a person skilled in the art knows that the relative quantification is rendered possible by means of the ratio of intensity of the diffraction lines:the height of the line at 27° 2 corresponding to the beta crystalline form in comparison with the height of the line at 20° 1 corresponding to the alpha form.

A mixture exhibiting, for example, 25% of alpha crystalline form and 75% of beta crystalline form gives a ratio of height of the lines of 21, whereas a mixture comprising 50% gives a value for ratio of lines of 5.

The coagglomerates in accordance with the invention having the characteristics mentioned above are capable of being obtained very particularly according to a process which comprises a step of spray-drying or of granulation of a mixture of mannitol and starch.

This aim had not been achieved to date by means of the processes known to a person skilled in the art and applicable both to mannitol and to starch. This is because the latter exhibits the disadvantage, when thermal processes in an aqueous medium are used, of cooking and of thus losing its granular nature.

In a first preferred embodiment of the process in accordance with the invention, the coagglomerates of crystalline mannitol and of starch are prepared by spray-drying or by granulation of a mixture of a mannitol solution and of starch, the starch being suspended in the mannitol solution.

In a second preferred embodiment of the process in accordance with the invention, the coagglomerates of crystalline mannitol and of starch are prepared by spray-drying or by granulation of a mixture of a mannitol solution and of dry starch, the starch being incorporated in the dry form in the spray-dryer or during the granulation step.

According to a first preferred form, it is possible to proceed according to the following steps:

a) preparing, at a temperature of between 45 and 65° C., a "solution" of mannitol and granular starch in which:
    the mannitol/starch ratio is between 99.5/0.5 and 50/50 and preferably between 95/5 and 70/30,
    the solids content is between 25 and 45% as dry weight,
  b) keeping said solution of mannitol and of starch at a temperature of between 45 and 65° C.,
  c) spray-drying said solution in an MSD-type spray-dryer equipped with a high pressure spray-drying nozzle with recycling of the fine particles at the spray-dryer top,
  d) recovering the coagglomerates of mannitol and of starch thus obtained.

The first step thus consists in preparing, at a temperature of between 45 and 65° C., the solution of mannitol and of granular starch in which:

the mannitol/starch ratio is between 99.5/0.5 and 50/50 and preferably between 95/5 and 70/30,
  the solids content is between 25 and 45% as dry weight.

While the initial particle size of the mannitol crystals is not an essential characteristic, the starch content is, on the contrary, an important parameter, as is its ratio to the mannitol.

A mannitol/starch ratio of between 99.5/0.5 and 50/50 and preferably between 95/5 and 70/30 is then chosen.

The second step consists in keeping said solution of mannitol crystals and of starch at the temperature of between 45 and 65° C.

Keeping at this temperature makes it possible to retain the mannitol in the dissolved state or in the forms of crystals of low particle size. The temperature is chosen so as to retain the starch in the granular form.

The third step then consists in spray-drying said solution in an MSD-type (i.e., Multi-Stage Dryer) spray-dryer equipped with a high pressure spray-drying nozzle with recycling of the fine particles at the spray-dryer top.

As will be seen in the examples below, the Applicant Company recommends the use of a MSD 20-type spray-dryer sold by Niro.

The spray nozzle is chosen so as to obtain a pressure of between 20 and 250 bar, for a flow rate of between 50 and 170 l/h, preferably of the order of 120 l/h.

The temperatures of the inlet airs are adjusted in the following way:

for the inlet air upstream of the spray-dryer top: temperature of between 120° C. and 240° C., for the static fluidized bed: temperature of between 50 and 120° C., for the vibrated fluidized bed: temperature of the order of 20° C.

The spray-dryer outlet temperature is then between 50 and 120° C.

The coagglomerates according to the invention are finally recovered at the outlet of the spray-dryer.

According to a second preferred form, it is possible to proceed according to the following steps:

a) preparing, at a temperature of between 45 and 90° C., a mannitol solution in which the solids content is between 25 and 50% as dry weight, b) keeping said mannitol solution at a temperature of between 45 and 90° C., c) spray-drying said solution in an MSD-type spray-dryer equipped with a high pressure spray-drying nozzle with recycling of the fine particles in the spray-dryer top, the dry starch being injected via a weight metering device into the system for recycling the fine particles in a mannitol/starch ratio of between 99.5/0.5 and 50/50 and preferably between 95/5 and 70/30, d) recovering the coagglomerates of mannitol and of starch thus obtained.

The Applicant Company has thus observed that the injection of the starch into the recycling system makes possible an intimate mixing with the mannitol during the drying.

The solution is spray-dried as in the preceding preferred form, in an MSD-type (i.e., Multi-Stage Dryer) spray-dryer equipped with a high pressure spray-drying nozzle with recycling of the fine particles at the spray-dryer top.

As will be seen in the examples below, the Applicant Company recommends using a MSD 20-type spray-dryer sold by Niro.

The spray nozzle is chosen so as to obtain a pressure of between 20 and 250 bar, for a flow rate of between 50 and 170 l/h, preferably of the order of 120 l/h.

The temperatures of the inlet airs are adjusted in the following way:

for the inlet air upstream of the spray-dryer top: temperature between 120° C. and 240° C., for the static fluidized bed: temperature of between 50 and 120° C., for the vibrated fluidized bed: temperature of the order of 20° C.

The spray-dryer outlet temperature is then between 50 and 120° C.

The coagglomerates according to the invention are finally recovered at the outlet of the spray-dryer.

According to a third preferred form, it is possible to proceed according to the following steps:

a) preparing, at a temperature of between 45 and 65° C., a solution of mannitol and of granular starch in which:

the mannitol/starch ratio is between 99.5/0.5 and 50/50 and preferably between 95/5 and 70/30, the solids content is between 25 and 45% as dry weight, b) keeping said solution of mannitol and starch at a temperature of between 45 and 65° C., c) granulating said solution by spraying in a fluidized air bed granulator, d) recovering the coagglomerates of mannitol and of starch thus obtained.

In order to carry out the granulation, it is possible, for example, to employ a continuous fluidized air bed granulator.

A circular continuous fluidized air bed granulator with a discharge pipe or plug-flow rectangular continuous fluidized air bed granulator can advantageously be chosen.

As will be seen in the examples below, the Applicant Company has chosen to employ a continuous fluidized air bed granulator with a classifier of AGT type sold by Glatt.

A better understanding of the invention will be obtained with the help of the following examples, which are meant to be illustrative and without implied limitation.

EXAMPLE 1

Preparation of Coagglomerates According to the Invention by Spray-Drying of the Mixture of a Mannitol Solution in which the Granular Starch is Suspended Different compositions of coagglomerates consisting of mannitol and of granular starch at ratios respectively of 99/1, 95/5, 90/10, 85/15 and 80/20 are prepared by spray-drying according to the invention.

Use is made of crystalline mannitol, sold by the Applicant Company under the name PEARLITOL® 50C, exhibiting a laser volume mean diameter of approximately 50 μm and of "extra white" corn starch.

A solution of mannitol and starch at the desired solids content is prepared by dissolving the crystalline mannitol in demineralized water at 55° C. and by suspending the extra white corn starch therein.

The stirring must make it possible to obtain a fluid and homogeneous solution devoid of lumps. The operating conditions for the manufacture of these coagglomerates in the MSD 20-type spray-dryer sold by Niro appear in the following table 1.

TABLE 1

| Coagglomerates according to the invention | Mannitol/ starch ratio | Total solids content (%) | Pressure (bar) | Nozzle (SPRAYING SYSTEM type SK) | Upstream air temp. (° C.) | Temp. of the static fluidized bed (° C.) | Outlet air temp. (° C.) |
|---|---|---|---|---|---|---|---|
| "A" | 99/1 | 30 | 42 | 60*21 | 175 | 77 | 66 |
| "B" | 95/5 | 31.6 | 70 | 60*21 | 200 | 80 | 72 |
| "C" | 90/10 | 32 | 50 | 60*21 | 170 | 70 | 50 |
| "D" | 85/15 | 33.6 | 50 | 60*21 | 228 | 80 | 89 |
| "E" | 80/20 | 32 | 50 | 56*21 | 200 | 80 | 63 |
| Control mannitol alone EP 1 138 661 | 100/0 | NS | NS | NS | NS | NS | NS |

During the modification of the starch content, the preparation of the coagglomerates in accordance with the invention requires more particularly adjustments in the choice of the nozzle, of the spray-drying pressure and of the air temperatures in order to obtain a similar mean particle size.

The characteristics of the coagglomerates of mannitol and of starch according to the invention are presented in the following table 2.

TABLE 2

| Coagglomerates according to the invention | Alpha/beta crystalline forms (%) | Tableting capacity (N) | Flow grade (s) | Laser particle size (D4, 3 μm) | Tapped density (g/ml) | Aerated density (g/ml) |
|---|---|---|---|---|---|---|
| "A" | 80/20 | 279 | 4-5 | 165 | 0.633 | 0.543 |
| "B" | 85/15 | 231 | 3-4 | 119 | 0.719 | 0.621 |
| "C" | 75/25 | 377 | 4-5 | 124 | 0.565 | 0.481 |
| "D" | 70/30 | 184 | 4-5 | 127 | 0.654 | 0.559 |
| "E" | 70/30 | 205 | 5-6 | 120 | 0.667 | 0.562 |
| Control mannitol alone EP 1 138 661 | Beta | 60 to 80 N | 5-7 | 101 to 126 | 0.70-0.71 | 0.53-0.54 |

The behavior of the mannitol coagglomerates according to the invention is entirely satisfactory in terms of tableting capacity and flow.

With low (1%) or higher (20%) starch contents, the coagglomerate according to the invention exhibits a high tableting capacity.

This high tableting capacity makes it possible to formulate tablets which retain a hardness and thus a cohesion which is sufficient after incorporation of a high content of active ingredient.

This is thus an essential and desired characteristic for a pharmaceutical excipient dedicated to tablets and hard gelatin capsules. Furthermore, the flow times measured are very short, which will make possible an industrial use at a very high throughput on tableting presses and capsule-filling machines.

EXAMPLE 2

Preparation of Coagglomerates According to the Invention by Spray-Drying of a Mannitol Solution and Incorporation of Granular Starch in the Dry Form in the Spray-Dryer.

Different compositions of coagglomerates consisting of mannitol and of starch at ratios respectively of 80/20, 70/30 and 50/50 are prepared by spray-drying according to the invention.

Use is made of crystalline mannitol, sold by the Applicant Company under the name PEARLITOL® 50C, exhibiting a laser volume mean diameter of approximately 50 μm and of "extra white" corn starch.

A mannitol solution at the desired solids content is prepared by dissolving the crystalline mannitol in demineralized water at 70° C.

The starch is introduced in the dry form in the recycling of the fine particles via a weight metering device sold by K-Tron.

The operating conditions for the manufacture of these coagglomerates in the MSD 20-type spray-dryer sold by Niro appear in the following table 3.

TABLE 3

| Coagglomerates according to the invention | Mannitol/ starch ratio | Solids content (%) | Pressure (bar) | Nozzle (SPRAYING SYSTEM type SK) | Upstream air temp. (° C.) | Temp. of the static fluidized bed (° C.) | Outlet air temp. (° C.) |
|---|---|---|---|---|---|---|---|
| "F" | 80/20 | 40 | 25 | 56*21 | 156 | 84 | 64 |
| "G" | 80/20 | 40 | 110 | 69*21 | 150 | 84 | 65 |
| "H" | 80/20 | 40 | 40 | 60*21 | 133 | 70 | 58 |
| "I" | 70/30 | 40 | 40 | 60*21 | 133 | 77 | 60 |
| "J" | 50/50 | 40 | 40 | 60*21 | 133 | 77 | 60 |

The conditions for the preparation of the coagglomerates H, I and J according to the invention show that, with the same parameters, the increase in the starch content reduces the mean particle size.

Those relating to the preparation of the coagglomerates F and G show that the greater the spray-drying pressure, the more the mean particle size decreases.

The characteristics of the coagglomerates of mannitol and of starch according to the invention are presented in the following table 4, in comparison with two physical mixtures P1 and P2:

the mixture P1 being composed of 80% of PEARLITOL® 50 C and of 20% of "extra white" starch, the mixture P2 being composed of 80% of PEARLITOL® 200 SD (sold by the Applicant Company) and 20% of "extra white" starch.

TABLE 4

| Coagglomerates according to the invention | Alpha/beta crystalline forms (%) | Tableting capacity (N) | Flow grade (s) | Laser particle size (D4, 3 μm) | Tapped density (g/ml) | Aerated density (g/ml) |
|---|---|---|---|---|---|---|
| "F" | 75/25 | 229 | 7-8 | 178 | 0.565 | 0.472 |
| "G" | 90/10 | 262 | 5-6 | 98 | 0.676 | 0.575 |
| "H" | 85/15 | 312 | 5-6 | 173 | 0.568 | 0.483 |
| "I" | 90/10 | 262 | 5 | 145 | 0.595 | 0.505 |
| "J" | 95/5 | 220 | 5 | 131 | 0.599 | 0.508 |
| Mixture of powders P1 | 0/100 | Impossible | 5 to 6 | 34 | 0.667 | 0.548 |
| Mixture of powders P2 | 50/50 | Impossible | Unlimited | 148 | 0.769 | 0.538 |

The behavior of the mannitol coagglomerates according to the invention is entirely satisfactory in terms of flow and tableting capacity.

It is possible to vary the production parameters in order to adjust the particle size and the density of the powder.

The homogeneity in mixture of an excipient and of an active ingredient depends on the mixing process employed but also on the similarity in the characteristics of the two powders.

It is easier to mix an active ingredient powder and an excipient powder when they exhibit the same particle size and the same density.

This explains the advantage of varying these characteristics and of having available a range of powders with different properties in order to be suitable for the various powders formed of active ingredients. Furthermore, it is possible to vary the starch content of the coagglomerate in order to adjust the tableting capacity to the product to be formulated without disturbing the noteworthy flow properties of the powder.

A simple physical mixture of powders (P1 and P2) does not make it possible to obtain the desired tablets.

EXAMPLE 3

Preparation of Coagglomerates According to the Invention by Granulation of the Mixture of a Mannitol Solution and of Starch, the Starch being Suspended in the Mannitol Solution Different compositions of coagglomerates consisting of mannitol and of starch at ratios respectively of 85/15, 70/30 and 50/50 are prepared by granulation according to the invention.

Use is made of crystalline mannitol, sold by the Applicant Company under the name PEARLITOL® 50C, exhibiting a laser volume mean diameter of approximately 50 μm and of "extra white" corn starch.

A solution of mannitol and of starch at the desired solids content is prepared by dissolving the crystalline mannitol in demineralized water at 55° C. and by suspending the extra white corn starch.

The stirring must make it possible to obtain a fluid and homogeneous solution devoid of lumps.

The operating conditions for the manufacture of these coagglomerates in the continuous fluidized air bed granulator of AGT 150 type sold by Glatt appear in the following table 5.

The spray nozzle is in the "bottom spray" position.

TABLE 5

| Coagglomerates according to the invention | Mannitol/ starch ratio | Total solids content (%) | Feed flow rate (g/h) | Air flow rate (m³/h) | Inlet air temp. (° C.) | Product bed temp. (° C.) | Nozzle spray pressure (bar) | Zig-zag classifier pressure (bar) |
|---|---|---|---|---|---|---|---|---|
| "K" | 70/30 | 38 | 2700 | 105 | 105 | 55 | 1.0 | 0.25 |
| "L" | 50/50 | 45 | 2140 | 85 | 100 | 58 | 1.0 | 0.3 |
| "M" | 85/15 | 34 | 4000 | 100 | 125 | 50 | 1.5 | 0.25 |
| "N" | 85/15 | 39 | 3700 | 100 | 125 | 62 | 1.5 | 0.3 |
| "O" | 85/15 | 34 | 3700 | 100 | 105 | 41 | 1.0 | 0.5 |

The characteristics of the coagglomerates of mannitol and of starch according to the invention are presented in the following table 6.

TABLE 6

| Coagglomerates according to the invention | Alpha/beta crystalline forms (%) | Tableting capacity (N) | Flow grade (s) | Laser particle size (D4, 3 μm) | Tapped density (g/ml) | Aerated density (g/ml) |
|---|---|---|---|---|---|---|
| "K" | 85/15 | 158 | 4 | 120 | 0.719 | 0.588 |
| "L" | 75/25 | 120 | 5-6 | 180 | 0.649 | 0.549 |
| "M" | 15/85 | 172 | 6 | 125 | 0.770 | 0.676 |
| "N" | 35/65 | 147 | 5-6 | 154 | 0.733 | 0.609 |
| "O" | 20/80 | 132 | 7 | 293 | 0.713 | 0.659 |

The results obtained demonstrate that, by granulation, coagglomerates in accordance with the invention are obtained which are equivalent to those obtained by spray-drying.

EXAMPLE 4

Preparation of Coagglomerates According to the Invention by Spray-Drying of the Mixture of a Mannitol Solution and of Granular Starch Introduced in the Dry Form in the Spray-Dryer Three coagglomerates consisting of mannitol and of starch at a ratio of 80/20 are prepared by spray-drying according to the invention with crystalline mannitol and three different granular starches, the "extra white" corn starch, potato starch and a hydroxypropylated stabilized and phosphate crosslinked waxy corn starch, sold by the Applicant Company under the name CLEARAM® CR 20/10.

The operating conditions for the manufacture of these coagglomerates appear in the following table 7.

TABLE 7

| Coagglomerates according to the invention | Starch suspended in the mannitol solution | Solids content (%) | Pressure (bar) | Nozzle (SPRAYING SYSTEM type SK) | Upstream air temp. (° C.) | Temp. of the static fluidized bed (° C.) | Outlet air temp. (° C.) |
|---|---|---|---|---|---|---|---|
| "H" | Extra white corn starch | 40 | 40 | 60*21 | 133 | 70 | 58 |
| "P" | Potato starch | 40 | 40 | 60*21 | 150 | 77 | 63 |
| "Q" | CLEARAM CR 20/10 | 40 | 40 | 60*21 | 150 | 77 | 63 |

The characteristics of the coagglomerates of mannitol and of starch according to the invention are presented in the following table 8.

TABLE 8

| Coagglomerates according to the invention | Alpha/beta crystalline forms (%) | Tableting capacity (N) | Flow grade (s) | Laser particle size (D4, 3 μm) | Tapped density (g/ml) | Aerated density (g/ml) |
|---|---|---|---|---|---|---|
| "H" | 85 | 312 | 5-6 | 173 | 0.568 | 0.483 |
| "P" | 90 | 227 | 4-5 | 165 | 0.654 | 0.556 |
| "Q" | 85 | 284 | 5-7 | 236 | 0.546 | 0.463 |

US 12,616,660 B2

15

The behavior of the mannitol coagglomerates according to the invention is entirely satisfactory with regard to tableting capacity and flow.

The replacement of the extra white corn starch by any other type of granular starch is possible while retaining essential characteristics of the product according to the invention.

It is thus possible to produce this agglomerate whatever the granular starch available to it and thus to be freed from the problems of availability, of regional culture, but also to take into account the wish or restrictions of consumers (absence of genetically modified organism) or of patients (wheat starch causing celiac disease).

A chemical modification of the starch in order to adjust its properties can also be carried out provided that the starch remains granular.

EXAMPLE 5

Filling of Hard Gelatin Capsules on an Automatic Capsule-Filling Machine of Dosing Disk Type, with a Coagglomerate According to the Invention and, in Comparison, with Two Mannitol Powders Sold by the Applicant Company The object of these tests is to determine the minimum lubricant content necessary for correct operation of the capsule-filling machine.

Magnesium stearate, which is the most widely used lubricant in the pharmaceutical field, is used for this.

A homogeneous mixture of the test powder and of magnesium stearate pharma veg from Barlöcher (Germany) is prepared. The amounts of test product and of magnesium stearate required to reach a final weight for the two of 300 g are placed in a jar with a capacity of 1 liter.

The two products are subsequently mixed for 5 min using a Turbula T2F epicyclic mixer from Willy A. Bachofen (Switzerland). The mixture thus produced is said to be lubricated.

The equipment used to fill said hard gelatin capsules is an In-Cap capsule-filling machine from Dott. Bonapace (Italy).

The chosen size of the hard gelatin capsules is the "2" format and all the components corresponding to this format are installed on the In-Cap capsule-filling machine.

Two dosing drum formats are possible on the In-Cap capsule-filling machine. The large model is used.

The compression pins are adjusted in the following way: pin 1=27.5 mm, pin 2=29 mm, pin 3=32 mm and pin 4=35 mm.

The distance expressed is that measured between the upper face of the nut for attaching each pin and the lower face of the nut for adjusting each pin.

Pin 1 is the first pin to go into operation. Pin 1 penetrates the deepest into the dosing disk and pin 4 penetrates the least deeply into the dosing disk. The dosing disk and the counterdisk have a thickness of 14.5 mm.

The hard gelatin capsule shells used are Coni-Snap ones from Capsugel (reference 2CS Natural Tr. Code 43.000).

The thickness of the powder bed in the dosing drum is adjusted in order to obtain hard gelatin capsules filled with the lubricated mixture and with a final weight of 310 mg.

The test is regarded as satisfactory if the production of a continuous series of 300 hard gelatin capsules is possible.

No interruption of any sort is tolerated during the production of these 300 hard gelatin capsules.

The hard gelatin capsules are not permanently closed in order to be able to open them again and thus observe the plugs present in them.

16

TABLE 9

| Test product | PEARLITOL ® 200SD | PEARLITOL ® 300DC | Agglomerate according to the invention |
| --- | --- | --- | --- |
| Weight of the powder incorporated in the hard gelatin capsule (mg) | 310 | 370 | 280 |
| Minimum content of lubricant (magnesium stearate) (%) | 3 | 3 | 1.5 |

The In-Cap capsule-filling machine cannot operate correctly with a magnesium stearate content of less than 3%, for the PEARLITOL® 200SD and the PEARLITOL® 300DC (two grades of mannitol sold by the Applicant Company), or of less than 1.5%, for the coagglomerates according to the invention.

The plugs become jammed in the dosing disk and the ejection pin has to exert an abnormally high force in order to push them into the body of the hard gelatin capsules.

This causes problems which range from a lack of uniformity in weight of the hard gelatin capsules, to frequent production shutdowns, up to damage to the capsule-filling machine.

The addition of a high content—3%—of magnesium stearate makes it possible to solve the problem in all cases but it causes a delay in the dissolution of the hard gelatin capsule and thus in the bioavailability of the active principle, to the detriment of the care provided to the patient.

This is because magnesium stearate is insoluble in water and, at this high concentration of 3%, it generates an insoluble barrier layer around the contents of the hard gelatin capsule, which insoluble barrier layer greatly slows down the dissolution of the hard gelatin capsule.

The coagglomerates according to the invention require only a low content of magnesium stearate; half of the preceding content. The insoluble barrier layer cannot be formed or is too fragile to limit the dissolution and the bioavailability of the active principle.

EXAMPLE 6

Filling of Hard Gelatin Capsules with Coagglomerates According to the Invention and an Active Principle, Paracetamol The equipment used to fill the hard gelatin capsules is a simulator fitted to an Instron (USA) universal tensile/compression machine. The simulator is a metal block pierced by a vertical cylindrical hole closed at the lower part by a moveable dovetail.

The internal diameter of this hole is slightly less than the internal diameter of a hard gelatin capsule shell of "0" format. The lower part of the metal block is designed to receive a support which holds the lower part of the shell of the hard gelatin capsule in the axis of the vertical hole.

A metal cylinder, referred to as piston, with a diameter slightly less than that of the vertical hole is used to tamp down the lubricated powder in the metal block and thus to form the plug.

A homogeneous mixture of the coagglomerate, the paracetamol (fine crystalline RHODAPAP® from Rhodia) and magnesium stearate pharma veg from Barlöcher (Germany) is prepared.

147.75 g (49.25%) of coagglomerate and 147.75 g (49.25%) of paracetamol are placed in a jar with a capacity of 1 liter. The two products are mixed for 5 min using a Turbula T2F epicyclic mixer from Willy A. Bachofen (Switzerland).

4.5 g (1.5%) of magnesium stearate are added and mixing is carried out for a further 5 min. The mixture thus produced is said to be lubricated.

The hard gelatin capsule shells of "0" format used originate from Laboratoire LGA (Bandol, France).

500 mg of lubricated mixture are introduced into the simulator. The piston responsible for tamping down the powder descends at a constant vertical speed of 20 mm per minute until the force applied to the lubricated mixture to form the plug is 600 N.

The plug, once formed, and after withdrawal of the moveable dovetail, is pushed by the piston into the lower part of the shell of the hard gelatin capsule.

The hard gelatin capsules are subsequently closed manually.

The disintegration time of the hard gelatin capsules thus prepared is measured according to the method recommended by the European Pharmacopoeia (E.P. 6.0, 01/2008:20901, 2.9.1. Disintegration of tablets and capsules) which measurement is carried out on 12 hard gelatin capsules.

TABLE 10

| Coagglomerate according to the invention | "A" | "H" | "I" | "J" | "P" | "Q" |
|---|---|---|---|---|---|---|
| Disintegration time (s) | 151 | 147 | 175 | 161 | 164 | 159 |

The paracetamol hard gelatin capsules thus prepared exhibit a very short disintegration time in water, of less than 3 minutes. This time is much less than 15 minutes, the disintegration time set by the European Pharmacopoeia for hard gelatin capsules.

These tests confirm that the coagglomerates according to the invention make it possible to achieve very short disintegration times.

EXAMPLE 7

Preparation of Tablets with Coagglomerates According to the Invention and in Comparison with a Mannitol Powder Sold by the Applicant Company The object of these tests is to determine the minimum content of lubricant necessary for correct operation of the tableting press. Magnesium stearate, which is the most widely used lubricant in the pharmaceutical field, is used for this.

A homogeneous mixture of the test powder and of magnesium stearate pharma veg from Barlöcher (Germany) is prepared.

The amounts of test product and of magnesium stearate required to reach a final weight for the two of 300 g are placed in a jar with a capacity of 1 liter.

The two products are subsequently mixed for 5 min using a Turbula T2F epicyclic mixer from Willy A. Bachofen (Switzerland). The mixture thus produced is said to be lubricated.

The tablets are prepared using a Frogerais AM laboratory alternating press, sold by Sviac (France), equipped with concave punches with a diameter of 13 mm. The tablets with convex faces and a diameter of 13 mm have a thickness of 6 mm and weight of 0.734 g.

Decreasing contents of magnesium stearate are tested: 1.2%, 1.0%, 0.8%, 0.6% and 0.4% (% expressed with respect to the mixture of the two powders).

The presence of sticking (a portion of the powder remains stuck to the surface of the punch after ejection of the tablet) and of jamming (the section of the tablets exhibits gouges) is observed. The minimum content of lubricant corresponds to the content at which neither of these two defects is observed.

For PEARLITOL® 200SD, a mannitol powder sold by the Applicant Company, this content is 1.2%. For the coagglomerates according to the invention, it is 0.6%.

A lower content of lubricant is favorable to the dissolution and to the bioavailability of the active principles; furthermore, it is a sign of greater ease in producing the tablets industrially.

Simple and easy lubrication makes it possible to achieve very high production rates without the risk of downgrading or shutdown as a result of problems of sticking or jamming.

EXAMPLE 8

Comparison of Coagglomerates According to the Invention and of Agglomerates of Mannitol and of Starch Produced in a Single Effect Spray-Dryer Agglomerates of crystalline mannitol and of granular starch at mannitol/starch ratios of 80/20 and 50/50 respectively are prepared in a single effect spray-dryer.

Use is made, for this, of crystalline mannitol, sold by the Applicant Company under the name PEARLITOL® 50C, exhibiting a laser volume mean diameter of approximately 50 µm and of "extra white" corn starch.

A solution of mannitol and of starch at the desired solids content is prepared by dissolving the crystalline mannitol in demineralized water at 55° C. and by suspending the extra white corn starch therein.

The stirring must make it possible to obtain a fluid and homogeneous solution devoid of lumps. The operating conditions for the manufacture of these agglomerates in the single effect spray-dryer sold by Niro (Niro Minor atomizer) are presented in the following table 11.

TABLE 11

| Agglomerates | Mannitol/ starch ratio | Total solids content (%) | Upstream air temp. (° C.) | Outlet air temp. (° C.) |
|---|---|---|---|---|
| "R" | 80/20 | 32 | 200 | 63 |
| "S" | 50/50 | 32 | 200 | 63 |

The characteristics of the agglomerates of mannitol and of starch thus prepared in a single effect spray-dryer are presented in the following table 12.

TABLE 12

| Agglomerates | Mannitol/starch ratio | Tableting capacity (N) | Flow grade (s) | Laser particle size (D4, 3 µm) | Tapped density (g/ml) | Aerated density (g/ml) |
|---|---|---|---|---|---|---|
| "R" | 80/20 | 45 | unlimited | 37 | 0.649 | 0.877* |
| "S" | 50/50 | — | unlimited | 43 | 0.685 | 0.877* |

* The flow in the order to obtain the funnel was helped using a rod in aerated volume.

In comparison with the behavior of the coagglomerates according to the invention, the behavior of the agglomerates of mannitol and of starch produced in a single effect spray-dryer is certainly not satisfactory in terms of compressibility and flow.

The low tableting capacity (agglomerate "R"), indeed nonexistent tableting capacity (agglomerate "S"), does not make it possible to formulate tablets which retain a hardness and thus a cohesion which is sufficient after incorporation of a high content of active principle.

Furthermore, the flow properties of the agglomerates "R" and "S" are so bad that they do not make it possible to measure a flow time (unlimited time according to the test B).

What is claimed is:

1. Coagglomerates consisting essentially of crystalline mannitol and granular starch, wherein the coagglomerates have:

a laser mean volume diameter D4,3 of between 100 and 250 μm, a ratio of mannitol/starch is between 99.5/0.5 and 50/50, and the mannitol is a mixture consisting of both alpha and beta crystalline forms, wherein the crystalline mannitol has a laser mean volume diameter of approximately 50 μm, and the coagglomerates have a tableting capacity from 200 N to 450 N and a flow grade between 3 and 15 seconds.

2. The coagglomerate as claimed in claim 1, wherein the mannitol/starch ratio is between 95/5 and 70/30.

3. The coagglomerate as claimed in claim 1, wherein:
an aerated density is between 0.400 and 0.750 g/ml, and
a tapped density is between 0.500 and 0.850 g/ml.

4. The coagglomerate as claimed in claim 1, wherein:
an aerated density is between 0.450 and 0.650 g/ml, and
a tapped density is between 0.550 and 0.750 g/ml.

5. The coagglomerate as claimed in claim 1, wherein the starch is selected from the group consisting of standard corn starch, extra white corn starch, and potato starch, taken alone or in combination.

6. The coagglomerate as claimed in claim 1, wherein the coagglomerate consists of said crystalline mannitol and said granular starch.

7. The coagglomerate as claimed in claim 1, wherein said granular starch is a native or modified starch having retained its granular structure.

8. The coagglomerate as claimed in claim 3, wherein the aerated density is between 0.450 and 0.650 g/ml.

9. The coagglomerate as claimed in claim 3, wherein the tapped density is between 0.550 and 0.750 g/ml.

\* \* \* \* \*